US00PP35064P2

(12) United States Plant Patent
Koning

(10) Patent No.: US PP35,064 P2
(45) Date of Patent: Mar. 21, 2023

(54) ***LAVANDULA* PLANT NAMED 'ANOUK DELUXE 16115'**

(50) Latin Name: *Lavandula stoechas*
Varietal Denomination: Anouk Deluxe 16115

(71) Applicant: L. KONING BEHEER B.V., Nuis (NL)

(72) Inventor: Lammert Koning, Nuis (NL)

(73) Assignee: L. KONING BEHEER B.V., Nuis (NL)

( * ) Notice: Subject to any disclaimer, the term of this patent is extended or adjusted under 35 U.S.C. 154(b) by 0 days.

(21) Appl. No.: 17/876,125

(22) Filed: Jul. 28, 2022

(51) Int. Cl.
*A01H 5/02* (2018.01)
*A01H 6/50* (2018.01)

(52) U.S. Cl.
USPC ..... Plt./445

(58) Field of Classification Search
None
See application file for complete search history.

*Primary Examiner* — Susan McCormick Ewoldt
(74) *Attorney, Agent, or Firm* — C. Anne Whealy

(57) ABSTRACT

A new and distinct cultivar of *Lavandula* plant named 'Anouk Deluxe 16115', characterized by its compact, upright and broadly spreading plant habit; freely branching growth habit; freely flowering habit; dark purple-colored flowers and bright purple-colored terminal flower bracts positioned on strong and erect peduncles; long flowering period; and good garden performance.

2 Drawing Sheets

Figure 1:
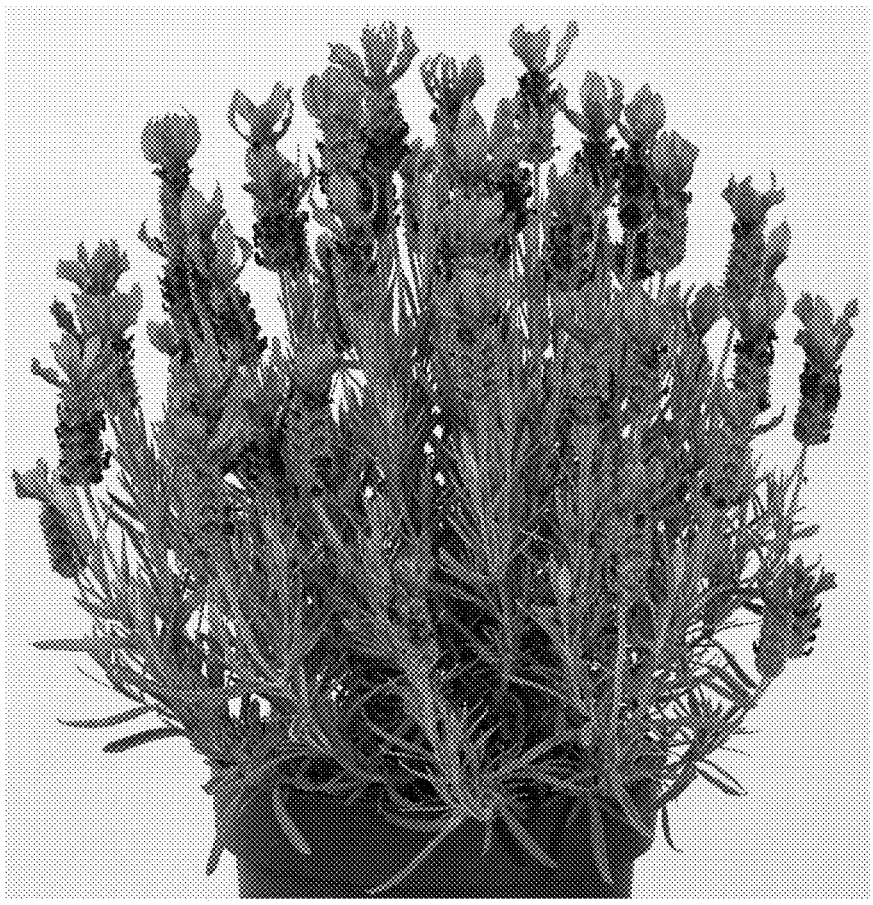

Botanical designation: *Lavandula stoechas.*
Cultivar denomination: 'ANOUK DELUXE 16115'.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 16115'.

The new *Lavandula* plant is a product of a planned breeding program conducted by the Inventor in Boskoop, The Netherlands. The objective of the breeding program was to develop new unique *Lavandula* plants with good performance and attractive plant form and flower coloration.

The new *Lavandula* plant originated from a cross-pollination in May, 2015 of *Lavandula stoechas* 'Anouk Deluxe 108', disclosed in U.S. Plant Pat. No. 31,930, as the female, or seed, parent with *Lavandula stoechas* 'Anouk Deluxe 1201', disclosed in U.S. Plant Pat. No. 28,265, as the male, or pollen, parent. The new *Lavandula* plant was discovered and selected by the Inventor as a single flowering plant within the progeny of the stated cross-pollination in a controlled environment in Boskoop, The Netherlands in July, 2016.

Asexual reproduction of the new *Lavandula* plant by terminal cuttings in a controlled greenhouse environment in Boskoop, The Netherlands since September, 2016 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 16115' as a new and distinct *Lavandula* plant:

1. Compact, upright and broadly spreading plant habit.
2. Freely branching growth habit.
3. Freely flowering habit.
4. Dark purple-colored flowers and bright purple-colored terminal flower bracts positioned on strong and erect peduncles.
5. Long flowering period.
6. Good garden performance.

Plants of the new *Lavandula* differ primarily from plants of the female parent, 'Anouk Deluxe 108', primarily in the following characteristics:

1. Plants of the new *Lavandula* are not as compact as plants of 'Anouk Deluxe 108'.
2. Plants of the new *Lavandula* have longer leaves than plants of 'Anouk Deluxe 108'.
3. Plants of the new *Lavandula* have darker purple-colored terminal flower bracts than plants of 'Anouk Deluxe 108'.

Plants of the new *Lavandula* differ primarily from plants of the male parent, 'Anouk Deluxe 1201', primarily in the following characteristics:

1. Plants of the new *Lavandula* have narrower leaves than plants of 'Anouk Deluxe 1201'.
2. Plants of the new *Lavandula* have darker purple-colored terminal flower bracts than plants of 'Anouk Deluxe 1201'.

Plants of the new *Lavandula* can be compared to plants of the *Lavandula stoechas* 'Anouk', disclosed in U.S. Plant Pat. No. 16,685. In side-by-side comparisons, plants of the new *Lavandula* differ primarily from plants of 'Anouk' in the following characteristics:

1. Plants of the new *Lavandula* are more compact than plants of 'Anouk'.
2. Leaves of plants of the new *Lavandula* are broader and more greyish green in color than leaves of plants of 'Anouk'.
3. Plants of the new *Lavandula* have darker purple-colored terminal flower bracts than plants of 'Anouk'.

Plants of the new *Lavandula* can also be compared to plants of the *Lavandula stoechas* 'Toscane', disclosed in U.S. Plant Pat. No. 18,046. In side-by-side comparisons, plants of the new *Lavandula* differ primarily from plants of 'Toscane' in the following characteristics:

1. Plants of the new *Lavandula* are more compact than plants of 'Toscane'.
2. Leaves of plants of the new *Lavandula* are broader and more greyish green in color than leaves of plants of 'Toscane'.
3. Plants of the new *Lavandula* have darker purple-colored terminal flower bracts than plants of 'Toscane'.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet (FIG. 1) is a side perspective view of a typical flowering plant of 'Anouk Deluxe 16115' grown in a container.

Figure 2:
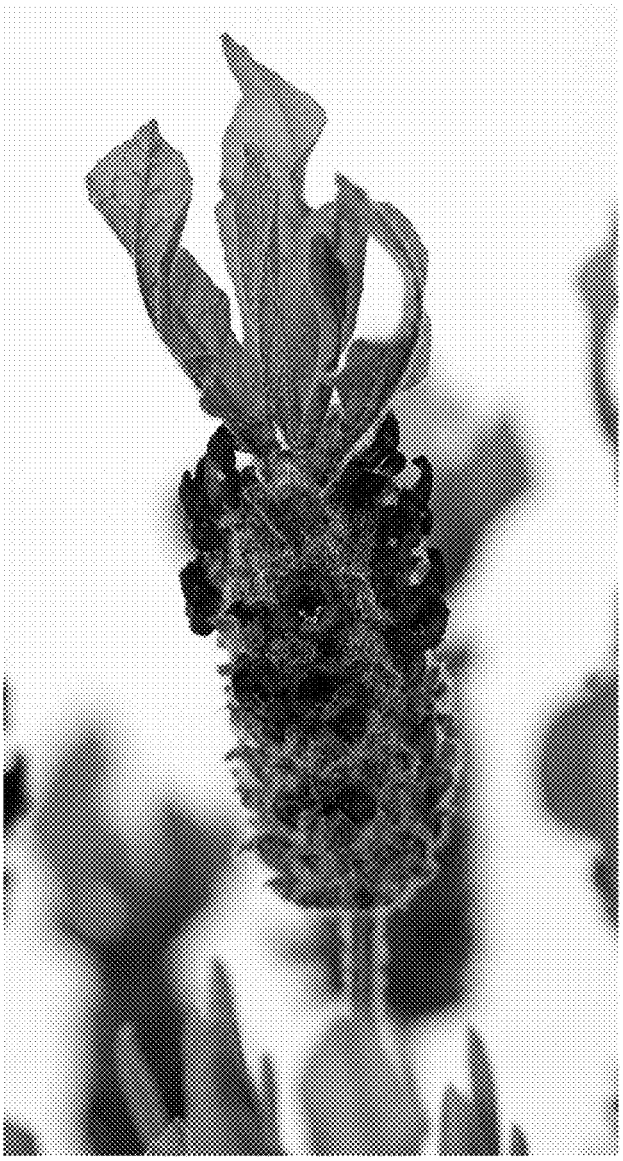

The photograph on the second sheet (FIG. 2) is a side perspective view of a typical inflorescence of 'Anouk Deluxe 16115'.

DETAILED BOTANICAL DESCRIPTION

Plants used in the aforementioned photographs and following detailed description were grown in 17-cm containers during the spring in a glass-covered greenhouse in Boskoop, The Netherlands and under cultural practices typical of commercial *Lavandula* production. Plants were pinched one time and were ten months old when the photographs and description were taken. During the production of the plants, day temperatures ranged from 10° C. to 30° C. and night temperatures ranged from 5° C. to 20° C. In the following description, color references are made to The Royal Horticultural Society Colour Chart, 2015 Edition, except where general terms of ordinary dictionary significance are used.

Botanical classification: *Lavandula stoechas* 'Anouk Deluxe 16115'.

Parentage:

*Female, or seed, parent.*—*Lavandula stoechas* 'Anouk Deluxe 108', disclosed in U.S. Plant Pat. No. 31,930.

*Male, or pollen, parent.*—*Lavandula stoechas* 'Anouk Deluxe 1201', disclosed in U.S. Plant Pat. No. 28,265.

Propagation:

*Type.*—Terminal vegetative cuttings.

*Time to initiate roots, summer and winter.*—About ten days at temperatures about 18° C.

*Time to produce a rooted young plant, summer.*—About 60 days at temperatures about 20° C.

*Time to produce a rooted young plant, winter.*—About 70 days at temperatures about 20° C.

*Root description.*—Fine, fibrous; initially white in color and becoming more brown with development; actual color of the roots is dependent on substrate composition, water quality, fertilizer type and formulation.

*Rooting habit.*—Freely branching; dense.

Plant description:

*Plant and growth habit.*—Herbaceous perennial; compact, upright and broadly spreading plant habit; globular to flattened globular in overall plant shape; freely branching habit; moderately vigorous growth habit; moderate growth rate; flowers arranged in verticillasters on crowded spikes with showy terminal flower bracts.

*Plant height, soil level to top of foliar plane.*—About 21.8 cm.

*Plant height, soil level to top of floral plane.*—About 27 cm.

*Plant width.*—About 35.8 cm.

*Lateral branch description.*—Quantity per plant: About seven primary lateral branches and about 60 secondary lateral branches developing per plant; pinching enhances branching potential. Length: About 9 cm. Diameter: About 1.75 mm. Internode length: About 1.6 cm. Strength: Moderately strong. Aspect: Primary lateral branches, upright to about 90° from vertical; secondary lateral branches, about 20° from primary lateral branch axis. Texture and luster: Moderately to densely tomentose; matte. Color, when developing: Close to 145A. Color, developed: Close to 143A and 145B; with development, close to 199A.

*Leaf description.*—Arrangement and quantity: Opposite, simple; sessile; about twelve leaves per lateral branch. Length: About 3.9 cm. Width: About 5 mm. Shape: Narrowly oblong to narrowly oblanceolate, flat. Apex: Acute. Base: Cuneate. Margin: Entire; slightly revolute; not lobed. Texture and luster, upper and lower surfaces: Moderately tomentose; not rugose; matte. Fragrance: Strongly aromatic, pungent. Venation pattern: Pinnate. Color: Developing leaves, upper surface: Close to 138A. Developing leaves, lower surface: Close to 137B. Fully expanded leaves, upper surface: Close to NN137C; venation, close to 146B. Fully expanded leaves, lower surface: Close to 137B; venation, close to 138B.

Flower description:

*Flower type, arrangement and habit.*—Small single salverform flowers arranged in compact verticillasters on crowded terminal spikes; freely flowering, about 100 flowers developing per inflorescence and more than 10,000 flowers developing per plant; flowers with two-lobed upper lip and three-lobed lower lip; flowers face mostly outwardly on the spike; inflorescences with showy terminal flower bracts.

*Natural flowering season.*—Long flowering period; continuous from late spring into the summer in The Netherlands; plants begin flowering about 13 weeks after planting.

*Flower longevity on the plant*.—Individual flowers last about four weeks on the plant; flowers not persistent.

*Fragrance*.—None detected.

*Flower buds*.—Length: About 7 mm. Diameter: About 2.5 mm. Shape: Elliptic. Texture and luster: Moderately tomentose; matte. Color: Close to 199A; towards the base, close to 145B to 145C; towards the apex, tinged with close to N186C and at the apex, close to 60B to 60C.

*Inflorescence size*.—Height, including terminal flower bracts: About 5 cm. Height, excluding terminal flower bracts: About 3 cm. Diameter, at terminal flower bracts: About 2.5 cm. Diameter, below flower bracts: About 1.6 cm.

*Flower size*.—Diameter: About 4 mm by 4 mm. Depth (height): About 8 mm. Throat diameter: About 1 mm. Tube length: About 6 mm. Tube diameter: About 1 mm.

*Petals*.—Quantity and arrangement: Upper lip, two-lobed and lower lip, three-lobed. Length, upper lip: About 7 mm. Length, lower lip: About 6 mm. Width, upper lip: About 2.5 mm. Width, lower lip: About 1.5 mm. Shape: Roughly spatulate; lower 72.5% fused into a tube. Apex: Obtuse. Margin: Entire; slightly undulate. Texture and luster, upper surface: Smooth, glabrous; velvety; not rugose; matte. Texture and luster, lower surface: Smooth, glabrous; moderately velvety; not rugose; slightly glossy. Texture, throat: Sparsely to moderately pubescent; matte. Texture, tube: Smooth, glabrous; matte. Color: When opening, upper and lower surfaces: Close to between N92A and N92C. Fully opened, upper and lower surfaces: Close to 83A to 83B; towards the margins, close to N92A to slightly darker than N92A; venation, similar to lamina colors; color becoming closer to N92A to slightly darker than N92A with subsequent development. Throat: Close to 83A to 83B; venation, close to 83A to 83B. Tube: Close to 83A to 83B fading proximally to close to N155D; venation, close to 83A to 83B fading proximally to close to N155D.

*Terminal flower bracts*.—Quantity and arrangement: About seven positioned upright at inflorescence apex. Length: About 2.2 cm. Width: About 8 mm. Shape: Narrowly obovate to oblanceolate. Apex: Broadly acute. Base: Narrowly cuneate. Margin: Entire; moderately to strongly undulate. Texture and luster, upper and lower surfaces: Slightly tomentose; matte. Color, upper surface: Close to N81B; midvein, close to 77A. Color, lower surface: Close to N80A; midvein, close to N79B.

*Basal flower bracts*.—Quantity and arrangement: Each group of five flowers is subtended by a single basal flower bract. Length: About 7 mm. Width: About 7 mm. Shape: Broadly rhomboidal. Apex: Aristate. Base: Cuneate. Margin: Irregularly dentate. Texture and luster, upper and lower surfaces: Densely tomentose; matte. Color, upper and lower surfaces: Close to 64C to 64D; venation, close to 147A and proximally, close to 146D.

*Sepals*.—Quantity and arrangement: Five, fused into a campanulate tube. Calyx length: About 5.5 mm. Calyx diameter: About 2 mm. Length: About 5.5 mm. Width: About 0.5 mm. Shape: Linear. Apex: Acute. Margin: Entire. Texture and luster, upper surface: Smooth, glabrous; matte. Texture and luster, lower surface: Densely pubescent; matte. Color: When opening, upper surface: Close to 145D; venation, close to 143B. When opening, lower surface: Close to 199A; towards the base, close to 145B to 145C; towards the apex, tinged with close to N186C and at the apex, close to 60B to 60C; venation, similar to lamina colors. Fully opened, upper surface: Close to 145D; venation, close to 143B. Fully opened, lower surface: Close to 145B; towards the base, close to 157D; towards the apex, strongly tinged with close to N186C and at the apex, close to 64B to 64C; venation, similar to lamina colors.

*Peduncles*.—Length: About 5.9 cm. Diameter: About 2 mm. Aspect: Mostly upright. Strength: Strong. Texture and luster: Moderately tomentose; matte. Color: Close to 143A and 145B; distally, tinged with close to between N186C and 200A.

*Reproductive organs*.—Stamens: Quantity per flower: Four. Filament length: About 1 mm. Filament color: Close to 83B. Anther shape: Reniform; dorsifixed. Anther size: About 0.5 mm by 0.5 mm. Anther color: Close to N92A. Pollen amount: Scarce. Pollen color: Close to 17B to 17C. Pistils: Quantity per flower: One. Pistil length: About 4 mm. Stigma shape: Club-shaped. Stigma diameter: About 0.5 mm. Stigma color: Close to N92A. Style length: About 3.5 mm. Style color: Close to 157D to lighter than 157D; proximally, close to 145D. Ovary color: Close to 144A.

*Seeds and fruits*.—To date, seed and fruit production has not been observed on plants of the new *Lavandula*.

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be suitable for USDA Hardiness Zones 7 to 10.

It is claimed:

1. A new and distinct *Lavandula* plant named 'Anouk Deluxe 16115' as illustrated and described.

* * * * *